US008585987B2

(12) United States Patent
Tseung et al.

(10) Patent No.: US 8,585,987 B2
(45) Date of Patent: *Nov. 19, 2013

(54) AUTOMATED TISSUE STAINING SYSTEM AND REAGENT CONTAINER

(75) Inventors: Ken K. Tseung, Fremont, CA (US); Norman K. Rhett, San Ramon, CA (US); Glenn K. Takayama, Danville, CA (US); Wai Bun Wong, Fremont, CA (US); Delia P. Yuen, Cupertino, CA (US)

(73) Assignee: Lab Vision Corporation, Fremont, CA (US)

( * ) Notice: Subject to any disclaimer, the term of this patent is extended or adjusted under 35 U.S.C. 154(b) by 0 days.
This patent is subject to a terminal disclaimer.

(21) Appl. No.: 13/429,518

(22) Filed: Mar. 26, 2012

(65) Prior Publication Data
US 2012/0219469 A1    Aug. 30, 2012

Related U.S. Application Data

(60) Continuation of application No. 13/041,608, filed on Mar. 7, 2011, now Pat. No. 8,142,739, which is a continuation of application No. 12/644,705, filed on Dec. 22, 2009, now Pat. No. 7,901,941, which is a division of application No. 12/250,116, filed on Oct. 13, 2008, now Pat. No. 7,642,093, which is a division of application No. 11/351,159, filed on Feb. 9, 2006, now Pat. No. 7,435,383, which is a division of application No. 09/994,458, filed on Nov. 26, 2001, now Pat. No. 6,998,270.

(51) Int. Cl.
*B01L 3/00* (2006.01)
*G01N 1/31* (2006.01)

(52) U.S. Cl.
USPC ........... 422/547; 422/549; 422/554; 422/556; 422/558; 435/288.1; 206/569; 220/604; 220/608; 215/370; 215/395; 215/399; 211/71.01; 211/74

(58) Field of Classification Search
USPC ......... 422/547, 549, 554, 556, 557, 558, 560, 422/561, 562; 435/288.1; 206/569; 220/600, 604, 608, 660, 669, 675; 215/382, 395, 399, 370; 211/85.13, 211/71.01, 74
See application file for complete search history.

(56) References Cited

U.S. PATENT DOCUMENTS

D226,846 S    5/1973  Rosenburg
3,897,216 A *  7/1975  Jones ............................ 422/561

(Continued)

FOREIGN PATENT DOCUMENTS

DE    9400010.7 U1    2/1994
DE    197 36 470 A1    3/1999

(Continued)

OTHER PUBLICATIONS

Biogenex, Optimax TM Automated Cell Staining System, 4 pages.

(Continued)

*Primary Examiner* — Maureen Wallenhorst
(74) *Attorney, Agent, or Firm* — Wood, Herron & Evans, LLP

(57) ABSTRACT

An automated staining system and a reagent container designed for use with the automated staining apparatus. The reagent container includes a reagent containment section capable of containing a volume of a reagent. The reagent containment section includes an upper wall and a base wall that are spaced apart along an axis. The base wall includes a well having a nadir that is aligned axially with an access opening in the upper wall so that a reagent probe entering the opening parallel to the axis will travel toward the nadir. In another aspect of the invention, the reagent container may include a two-dimensional data element containing reagent information. The staining apparatus may include one removable drawer for holding reagent containers and another removable drawer holding slides.

5 Claims, 7 Drawing Sheets

(56) References Cited

U.S. PATENT DOCUMENTS

| | | |
|---|---|---|
| 3,912,456 A | 10/1975 | Young |
| 4,141,312 A | 2/1979 | Louder et al. |
| 4,605,126 A | 8/1986 | Goedken et al. |
| 4,793,491 A | 12/1988 | Wolf et al. |
| 4,794,239 A | 12/1988 | Allais |
| 4,874,936 A | 10/1989 | Chandler et al. |
| 4,896,029 A | 1/1990 | Chandler et al. |
| 4,939,354 A | 7/1990 | Priddy et al. |
| 4,998,010 A | 3/1991 | Chandler et al. |
| 5,009,942 A | 4/1991 | Benin et al. |
| 5,053,609 A | 10/1991 | Priddy et al. |
| 5,073,504 A | 12/1991 | Bogen |
| 5,116,759 A | 5/1992 | Klainer et al. |
| 5,124,536 A | 6/1992 | Priddy et al. |
| 5,199,570 A | 4/1993 | McKenzie |
| 5,243,655 A | 9/1993 | Wang |
| 5,264,182 A | 11/1993 | Sakagami |
| 5,355,439 A | 10/1994 | Bernstein et al. |
| 5,417,121 A | 5/1995 | Andersen et al. |
| 5,425,918 A | 6/1995 | Healey et al. |
| 5,428,690 A | 6/1995 | Bacus et al. |
| 5,439,649 A | 8/1995 | Tseung et al. |
| 5,482,839 A | 1/1996 | Ashihara et al. |
| 5,523,047 A | 6/1996 | Corby et al. |
| 5,573,727 A | 11/1996 | Keefe |
| 5,595,707 A | 1/1997 | Copeland et al. |
| 5,650,327 A | 7/1997 | Copeland et al. |
| 5,654,199 A | 8/1997 | Copeland et al. |
| 5,654,200 A | 8/1997 | Copeland et al. |
| 5,670,117 A | 9/1997 | Erb et al. |
| 5,696,887 A | 12/1997 | Bernstein et al. |
| 5,793,969 A | 8/1998 | Kamentsky et al. |
| 5,800,784 A | 9/1998 | Horn |
| 5,839,091 A | 11/1998 | Rhett et al. |
| 5,854,075 A | 12/1998 | Levine et al. |
| 5,919,553 A | 7/1999 | Kavanaugh |
| 5,930,461 A | 7/1999 | Bernstein et al. |
| 5,948,359 A | 9/1999 | Kalra et al. |
| 6,027,695 A | 2/2000 | Oldenburg et al. |
| 6,045,759 A | 4/2000 | Ford et al. |
| 6,047,846 A | 4/2000 | Watson |
| 6,093,574 A | 7/2000 | Druyor-Sanchez et al. |
| 6,192,945 B1 | 2/2001 | Ford et al. |
| 6,296,809 B1 | 10/2001 | Richards et al. |
| 6,349,264 B1 | 2/2002 | Rhett et al. |
| 6,352,861 B1 | 3/2002 | Copeland et al. |
| 6,550,894 B2 * | 4/2003 | Ueno et al. ............ 347/49 |
| 6,735,531 B2 | 5/2004 | Rhett et al. |
| 6,746,851 B1 | 6/2004 | Tseung et al. |
| 6,800,249 B2 | 10/2004 | de la Torre-Bueno |
| 6,998,270 B2 | 2/2006 | Tseung et al. |
| 7,435,383 B2 | 10/2008 | Tseung et al. |
| 7,642,093 B2 | 1/2010 | Tseung et al. |
| 7,901,941 B2 | 3/2011 | Tseung et al. |
| 8,142,739 B2 * | 3/2012 | Tseung et al. ............ 422/547 |
| 2004/0009098 A1 | 1/2004 | Torre-Bueno |

FOREIGN PATENT DOCUMENTS

| | | |
|---|---|---|
| EP | 0 106 662 A2 | 4/1984 |
| EP | 0 510 686 A2 | 10/1992 |
| EP | 0 987 181 A2 | 3/2000 |
| GB | 2 216 259 A | 10/1989 |
| WO | 9113335 A1 | 9/1991 |
| WO | 9201919 A1 | 2/1992 |
| WO | 9828075 A1 | 7/1998 |
| WO | 0063696 A1 | 10/2000 |
| WO | 0151909 A1 | 7/2001 |

OTHER PUBLICATIONS

Biotek TM Solutions, Automated Immunostaining Systems, 1993, 13 pages.
Hamilton, MicrolabRTM SPE, 2 pages.
Leica Instruments GmbH, Automated Tissue Staining for Immunohistochemistry, Feb. 6, 1992, 8 pages.
Matrix Technologies Corporation, Automated Sample Handling, Sep. 1993, 4 pages.
Packard, MultiprobeRTM Robotic Liquid Handling, 8 page newsletter and pp. 8-9.
Rosys Inc., Introduce a new philosophy into your laboratory!, 1 page.
Sakura World Class Technology TM, RSG-61 Hematology Slide Stainer, 1995, 2 pages.
Shandon Inc., Shandon Clipshaw Cadenza Automated Immunostainer, 1989, pp. 1-8.
Tecan US, Inc., Progressing as One in Laboratory Automation, 10 page brochure.
Ventana, Ventana in Situ Hybridization System, Rev-Mar. 31, 1994, 1 page.
WIPO, Partial Search Report, PCT/US02/37552 dated Mar. 19, 2003, 2 pages.
Beckman, Biomek 2000 Automated Workstation, Undated, 1 page.

* cited by examiner

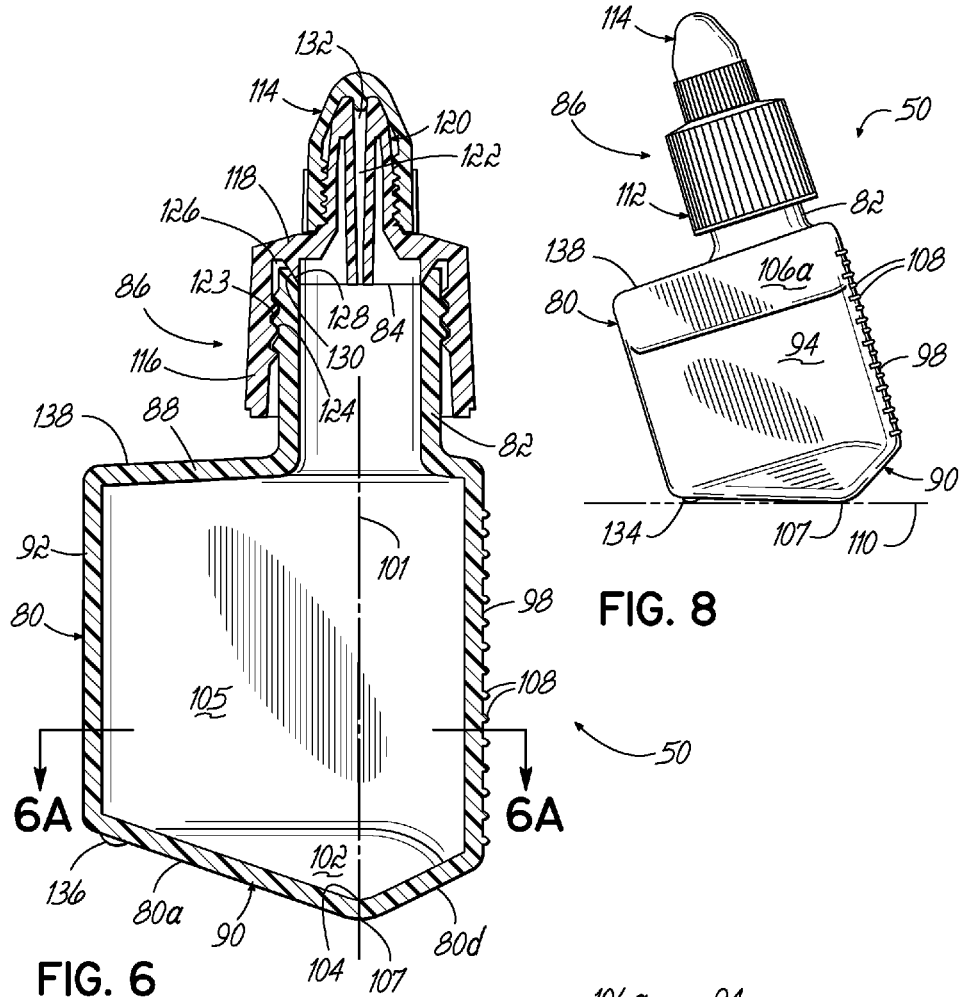
FIG. 6
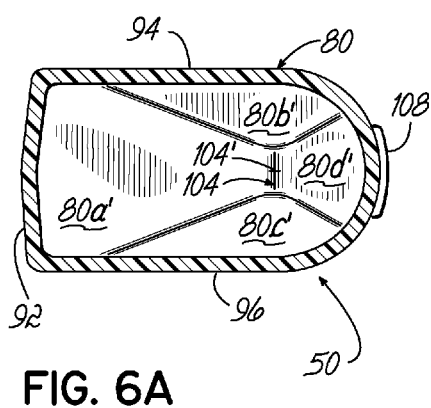
FIG. 6A
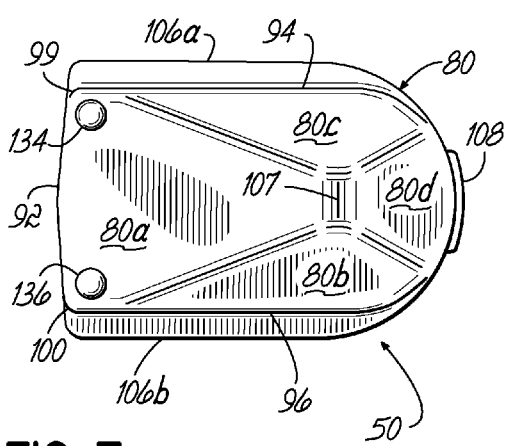
FIG. 7
FIG. 8

AUTOMATED TISSUE STAINING SYSTEM AND REAGENT CONTAINER

CROSS-REFERENCE

This application is a continuation of U.S. patent application Ser. No. 13/041,608, filed Mar. 7, 2011, now issued as U.S. Pat. No. 8,142,739 on Mar. 27, 2012, which is a continuation of U.S. patent application Ser. No. 12/644,705, filed Dec. 22, 2009, now issued as U.S. Pat. No. 7,901,941 on Mar. 8, 2011, which is a divisional of U.S. patent application Ser. No. 12/250,116, filed Oct. 13, 2008, now issued as U.S. Pat. No. 7,642,093 on Jan. 5, 2010, which is a divisional of U.S. patent application Ser. No. 11/351,159, filed Feb. 9, 2006, now issued as U.S. Pat. No. 7,435,383 on Oct. 14, 2008, which is a divisional of U.S. patent application Ser. No. 09/994,458, filed Nov. 26, 2001, now issued as U.S. Pat. No. 6,998,270 on Feb. 14, 2006, the disclosures of which are hereby incorporated herein by reference in their entireties.

FIELD OF THE INVENTION

The invention relates generally to an automated tissue staining system and reagent containers for use with the system.

BACKGROUND OF THE INVENTION

Laboratories routinely stain tissue specimens for the purpose of detecting and/or monitoring tissue abnormalities. An automated tissue staining system allows batch staining of large numbers of tissue specimens for subsequent examination. Automation of the staining process significantly reduces the time required to stain tissue specimens, reduces the incidence of human error incipient in manual staining, and allows processing parameters to be altered in an efficient manner.

The staining process requires various types of reagents that are added to a slide carrying a tissue specimen. Reagents are an expensive expendable commodity. In a typical automated staining apparatus, the reagents are typically aspirated with a reagent probe from a reagent container and delivered to the tissue specimen on each slide. For accurate reagent dispensing, the reagent container contains an excess volume of reagent beyond a volume required for the staining process. The excess volume is required so that the reagent probe can aspirate the required volume from the reagent container. Conventional reagent containers are not configured to optimize the amount of reagent that the reagent probe successfully can withdraw and, thereby, to minimize the amount of reagent wasted.

A conventional automatic staining apparatus typically requires a set-up sequence to enter reagent parameters such as lot number, reagent identity, expiration date, reagent volume, reagent incompatibilities, and the like. Some reagent containers have a one-dimensional bar code that contains this or a subset of this reagent information. Reading the reagent information with a bar code reader and providing that information to the control system operating the staining apparatus reduces the time required to program a staining run. However, one-dimensional bar codes capable of holding a complete set of reagent parameters are too large to be placed on the reagent containers commonly used in automatic staining apparatus.

The automated staining apparatus has a processing space in which the environment is tightly controlled during the staining run. If additional slides are to be added to the pending slides in a staining run, the user must pause the staining run and breach the controlled environment of the processing space to add the new slides. The reagent containers are also positioned within the processing space. If new slides are added, the user must modify the types and/or quantities of reagents to satisfy the requirements of the global staining protocols of all slides by again breaching the processing space. Therefore, the lab technician compromises or otherwise disrupts the integrity of the controlled environment in the processing space when slides are added to a currently executing staining run.

During a staining run, the tissue specimens are exposed to a series of well-defined processing steps or a protocol that ultimately produces a properly stained specimen for examination. Conventionally, the automated staining apparatus may store the protocol or, in the alternative, may memorialize the protocol by a printed hard copy. Conventional automated staining devices cannot provide or export the protocol directly to a patient record database or laboratory information system so that, should a question arise regarding the protocol used to stain a specific tissue specimen, the complete association is readily available in a single database.

SUMMARY OF THE INVENTION

According to the present invention, apparatus and methods are provided for staining tissue specimens using an autostainer. A reagent container capable of containing a volume of a reagent for use with the automated staining apparatus, which container includes an upper wall, a base wall and a tubular side wall interconnecting the upper and base walls to collectively define an internal reagent holding chamber, the upper and base walls being spaced from each other along an imaginary line intersecting the upper and base walls. The base wall includes a cavity communicating with the lowermost portion of the holding chamber. The upper wall has an access opening in the upper wall aligned with the cavity along the imaginary line so that a reagent probe entering the opening parallel in a direction to said imaginary line will travel toward said cavity bottom, the lowermost portion of said holding chamber.

In another aspect of the invention, the reagent container may include a two-dimensional data element containing reagent information. In yet another aspect of the invention, the staining apparatus may include a removable drawer for holding a reagent rack filled with reagent containers and a separate removable drawer holding slide racks.

These and other advantages, objectives, and features of the invention will be apparent in light of the following figures and detailed description.

BRIEF DESCRIPTION OF THE DRAWINGS

FIG. 1A is a diagrammatic view of the Z-head of FIG. 1.

FIG. 6 is a cross-sectional view of one of the reagent containers of FIG. 1.

FIG. 6A is a cross-sectional view taken generally along line 6A-6A of FIG. 6.

FIG. 7 is a bottom view of the reagent container of FIG. 6.

FIG. 8 is a side view of the reagent container of FIG. 6, shown positioned on a flat surface.

DETAILED DESCRIPTION

To remedy the aforementioned deficiencies of conventional automated tissue staining devices, the present invention provides an apparatus for automatically staining tissue specimens carried by slides according to various staining protocols and a reagent container that significantly reduces the amounts of wasted reagents. As used hereinafter, the term "staining" includes, but is not limited to, reagent uptake, chemical reaction, localization (e.g., antigen-antibody associations), radioactive activation, and the like.

Figure 1:
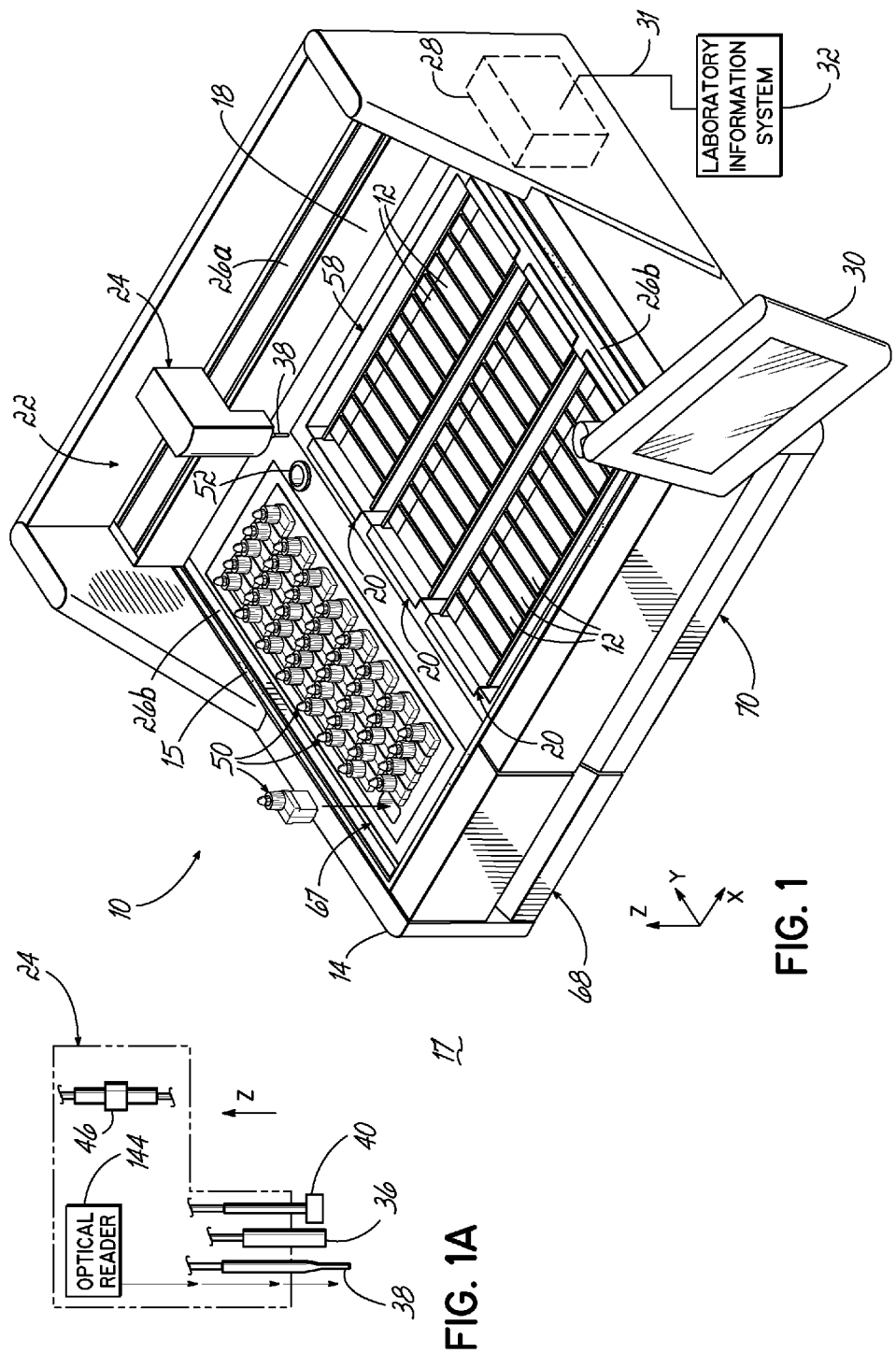
FIG. 1 is a perspective view of an automatic staining apparatus of the present invention, shown with the lid removed.
Figure 2:
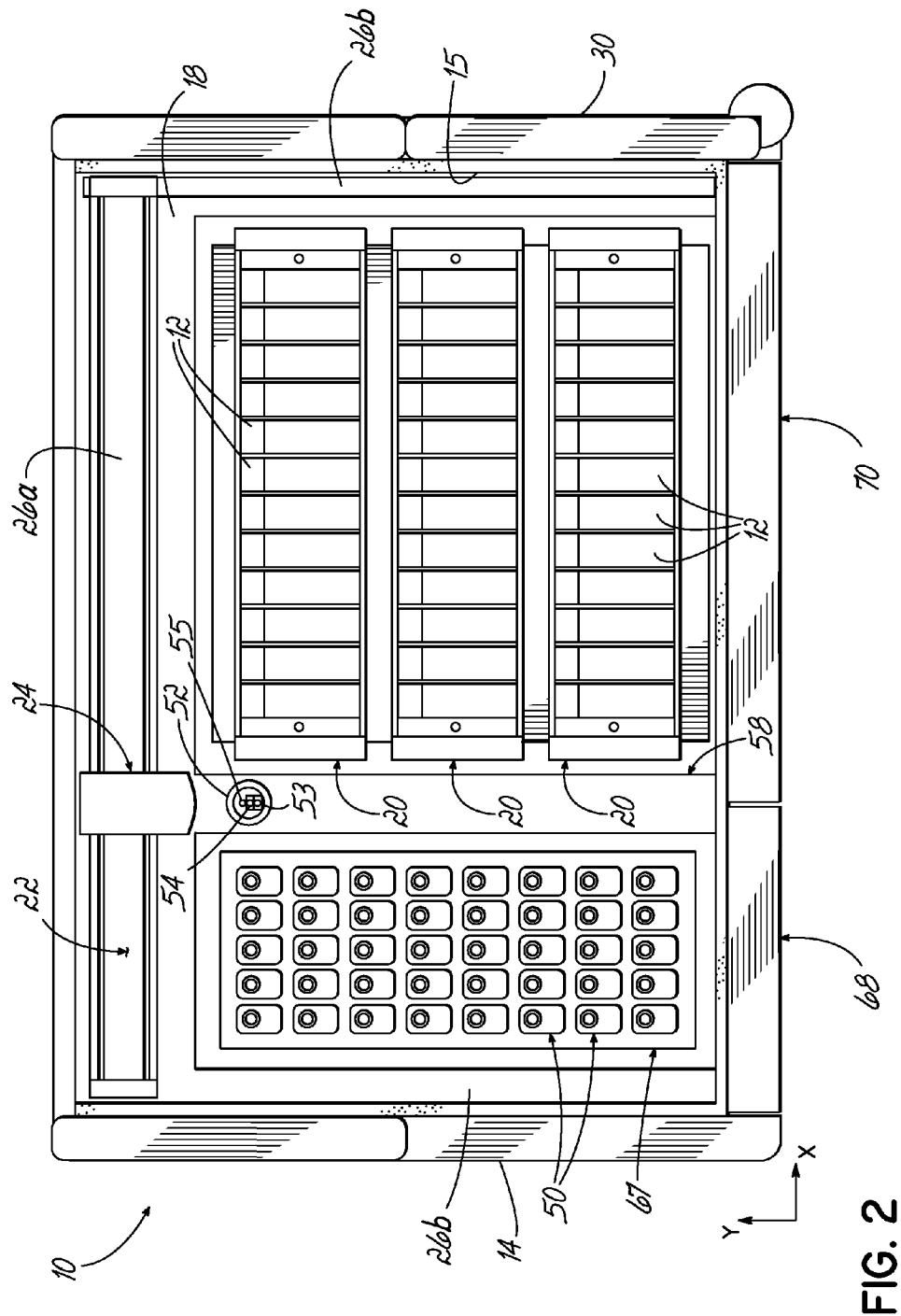
FIG. 2 is a top view of the automatic staining apparatus of FIG. 1.
Figure 3:
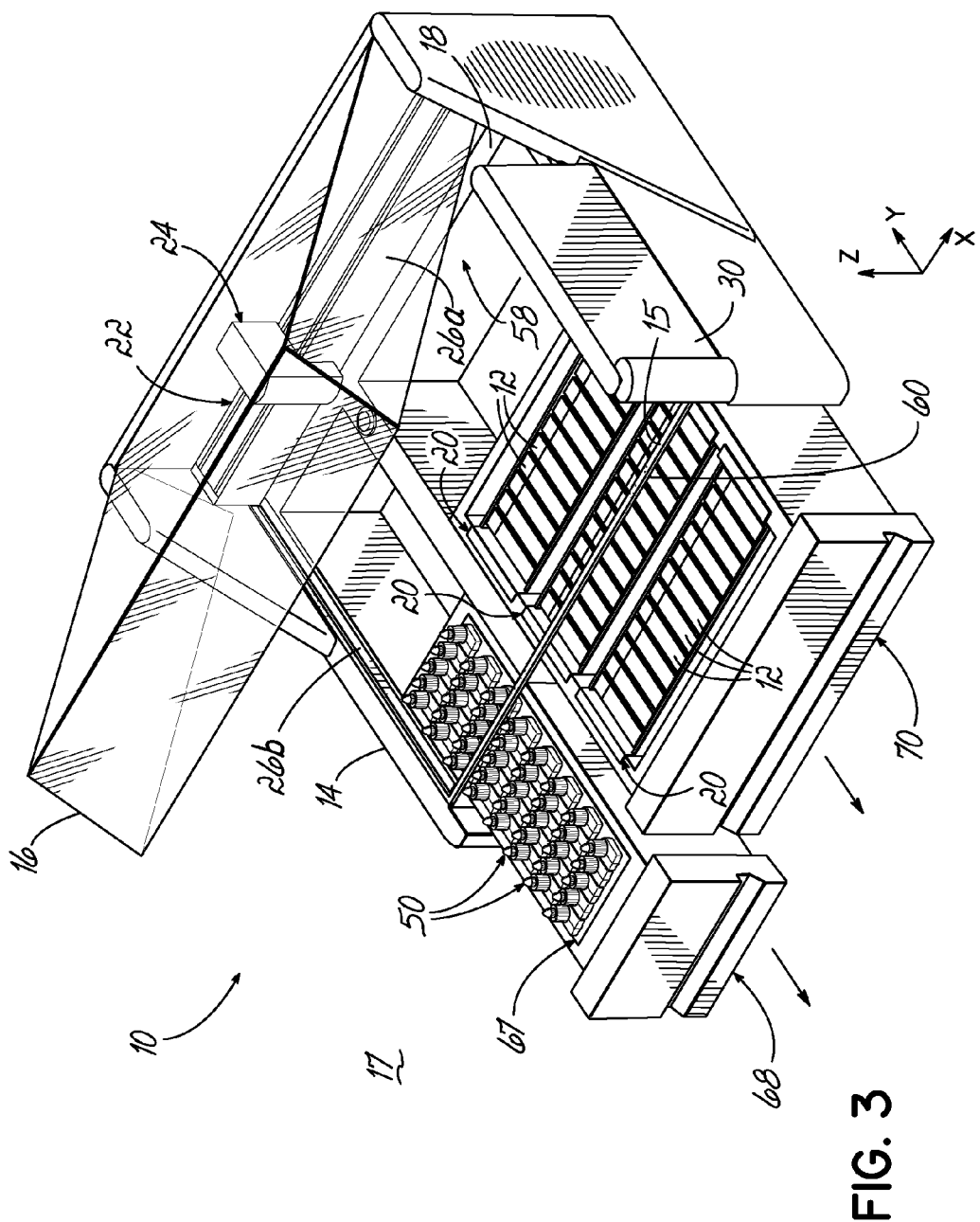
FIG. 3 is a perspective view of the automatic staining apparatus of FIG. 1, shown with the slide and reagent drawers withdrawn.

With reference to FIGS. 1, 2, and 3, the present invention comprises an automatic staining apparatus or autostainer 10 used for staining or otherwise reacting reagents with the cells of tissue specimens mounted on slides 12. The autostainer 10 includes a chassis 14 and a cover or lid 16 (FIG. 3), hinged along its rear horizontal edge, that collectively define a processing space 18 having a controlled environment, such as a controlled humidity. The lid 16 isolates the controlled environment of the processing space 18 from the surrounding ambient environment 17. Lid 16 may be optically transparent so that a user can observe events transpiring in the processing space 18. The lid 16 may also be hinged for cantilevering or moving the lid 16 between an open condition, indicated in solid lines in FIG. 3, and a closed condition, shown in phantom in FIG. 3. The lid 16 makes a sealing engagement with a seal 15 provided on the chassis 14 so as to participate in providing the controlled environment in processing space 18.

A plurality of slides 12 are held by a plurality of, for example, three slide racks 20 mounted in the processing space 18. Each of the three slide racks 20 holds, for example, twelve individual slides 12 so that the automatic staining apparatus can stain one or more tissue specimens mounted on a total of thirty-six slides 12. Typically, the clips (not shown) for holding the slides 12 contact only an unused region thereof, such as a frosted marginal region.

With continued reference to FIGS. 1, 2, and 3, the autostainer 10 includes an X-Y-Z robotic delivery system 22 that is capable of delivering bulk reagents, small supply reagents, buffer solutions, and air to the tissue specimens on the slides 12. The X-Y-Z robotic delivery system 22 includes a Z-head 24 that is controllably and selectively movable on a pair of linear motion assemblies, indicated generally by reference numerals 26a and 26b to any position in a horizontal X-Y plane. The Z-head 24 carries a vertically disposed probe 38, which is selectively and controllably movable up and down in a vertical, or Z, direction. An exemplary X-Y-Z robotic delivery system, similar to delivery system 22, is described in commonly-assigned U.S. Pat. No. 5,839,091 and in copending, commonly assigned U.S. patent application Ser. No. 09/483,248, filed on Jan. 14, 2000, now U.S. Pat. No. 6,746,851, and entitled "Method and Apparatus for Automatic Tissue Staining," the disclosure of each being expressly incorporated by reference herein in its entirety.

The operation of the autostainer 10, including the operation of the robotic delivery system 22, is controlled by an autostainer control program implemented by the software of a control system 28. The hardware of the control system 28 is integrated into the chassis 14 of the autostainer 10 and includes a touchscreen display 30. Touchscreen display 30 is a computer input device for viewing information and inputting information, as understood by those of ordinary skill in the art. Alternatively, various items of information may be viewed and entered remotely from the chassis 14. Because the control system 28 is integrated into the chassis 14, the autostainer 10 does not require an external microprocessor, such as a conventional personal computer, for operation and constitutes a self-contained stand-alone unit.

The control system 28 includes a data storage unit or medium for storing information, such as staining protocols, and retrieving that stored information on demand. The control system 28 is interfaced by a communication link 31, such as a local area network, so that the autostainer 10 may exchange information with another information storage device 32, such as another laboratory instrument or a remote computer system. For example, the control system 28 may be capable of exporting a staining record containing information such as the staining protocol, reagent information, and the like to the information storage device 32 over the communications link 31. The information storage device 32 would associate the staining record with existing patient information in a patient record database or a laboratory information system and provide, associate, and/or store the staining record with that information for future report generation. The information storage device may also perform statistical analysis on multiple staining records to, for example, determine compliance with regulatory standards.

The control system 28 is also capable of importing or retrieving information from the information storage device 32 via communications link 31. The imported information may comprise a staining record containing protocol information that the control system 28 can use as a template for staining one or more of the slides 12. The ability to import the staining protocol from device 32 precludes manually inputting the information using touchscreen display 30. The imported information may also include patient information, which may be associated with the staining protocol and/or stored by the control system 28. One use for the associated patient record and staining protocol, whether residing on control system 28 or on information storage device 32, is quality control and quality assurance documentation.

Figure 4:
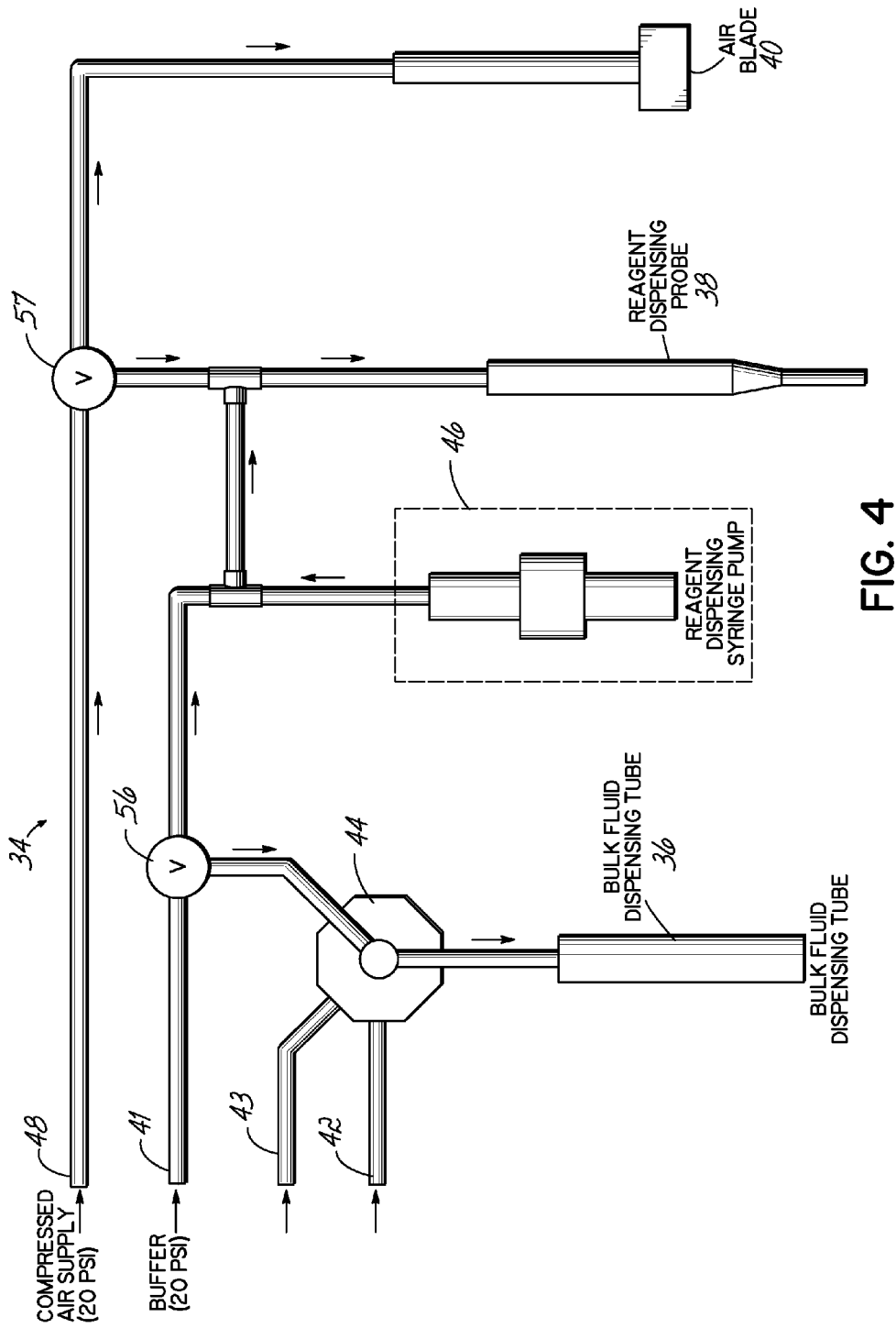
FIG. 4 is a diagrammatic view of the fluid dispensing system for the automatic staining apparatus of FIG. 1.

With reference to FIGS. 1, 1A and 4, the Z-head 24 of the robotic delivery system 22 carries a fluid dispensing system 34 having a bulk fluid dispensing tube 36, a reagent probe 38, and an air blade 40. The bulk fluid dispensing tube 36 is capable of dispensing buffer solution from a buffer supply (not shown) delivered by supply line 41 or reagents delivered via supply lines 42 and 43 from internal bulk reagent supplies (not shown), as selected by a distribution valve 44. The reagent probe 38 is capable of aspirating a small quantity of a specific reagent from one of a plurality of reagent containers 50 using suction generated by a reagent syringe pump 46 and then dispensing that reagent at a specific location on a specific slide 12. Air blade 40 is capable of selectively directing a flow of air delivered by supply line 48 from a compressed air supply (not shown) used to dry slides 12.

The Z-head 24 of the robotic delivery system 22 is equipped with a vertical drive assembly (not shown) operably coupled with the reagent probe 38 for controllably and selectively moving the probe 38 up and down in the vertical Z-direction. The vertical positions of the air blade 40 and the bulk fluid dispensing tube 36 are independently movable in the vertical Z-direction using a different vertical drive assembly (not shown) also disposed within the Z-head 24. The vertical drive assemblies are utilized to position the bulk fluid dispensing tube 36, reagent probe 38, and air blade 40 relative to the slides 12 and to position the reagent probe 38 relative to a wash bin 52 (FIGS. 1-3). A procedure for cleaning the reagent probe 38 using wash bin 52 is described in U.S. Pat. No. 5,839,091 incorporated by reference above.

With reference to FIGS. 1 and 2, the reagent probe 38 is cleaned in the wash bin 52 to remove residual traces of a reagent when a different reagent is to be aspirated from one of the reagent containers 50 and dispensed onto one or more of the slides 12. The practice of cleaning the reagent probe 38 lessens or eliminates the likelihood of cross-contamination and may be incorporated as process steps into the programming of the control system 28 of the autostainer 10. The wash bin 52 has three individual receptacles 53, 54, and 55 used in a sequence of three wash stages. The operation of wash bin 52 for cleaning the reagent probe 38 is described in U.S. Pat. No. 5,839,091 incorporated by reference above. Liquid waste, such as spent reagents and buffer rinse solution that drain from the slides 12, is captured by a sink assembly 58.

The autostainer control system 28 implements software that accepts and effectuates a series of process steps or staining protocol for staining the tissue specimen mounted on each slide 12. The autostainer 10 optimizes the order of protocol execution and executes the staining protocols by providing a series of instructions to the robotic delivery system 22. The execution may be paused to add slides 12 carrying prioritized or "stat" tissue specimens to the slide racks 20 and to integrate their staining protocols with the staining protocols of the slides 12 pending when the staining process was paused. Such protocol programming is described in U.S. Pat. No. 5,839,091 and patent application Ser. No. 09/483,248, now U.S. Pat. No. 6,746,851, incorporated by reference above, and in commonly assigned U.S. patent application Ser. No. 10/010,830, now U.S. Pat. No. 6,735,531, entitled "Method and Apparatus for Automatic Tissue Staining," which is expressly incorporated by reference herein in its entirety.

With reference to FIGS. 1-3 and 5, each of the small supply reagents is contained within one of the reagent containers 50. The reagent containers 50 are held in a reagent rack 67 that is disposed within a reagent drawer 68. Similarly, the slide racks 20 and sink assembly 58 are held within a slide drawer 70. The reagent drawer 68 and the slide drawer 70 are each independently slidably mounted for selective "in" and "out" movement in the Y-direction in a conventional manner relative to the chassis 14, such as with drawer slides. Reagent drawer 68 has a closed position (FIG. 1) in which the reagent containers 50 are positioned in the processing space 18 and an open position (FIG. 3) in which the reagent rack 67 is positioned outside of the processing space 18 and accessible externally of the chassis 14. A portion of seal 15 is suspended on a horizontal frame member 60 (FIG. 3) extending between the opposite side edges of the chassis 14.

As illustrated in FIG. 2, the reagent drawer 68 may be horizontally withdrawn in the Y direction from the closed position (FIG. 1) to the open position (FIG. 3) so as to permit access to the reagent rack 67. The withdrawal of the reagent drawer 68 may be accomplished manually or with the assistance of an actuator. This permits reagents to be added to individual reagent containers 50 already positioned in the reagent rack 67 and/or new reagent containers 50 to be added to rack 67. Alternatively, the reagent rack 67 may be removed from the reagent drawer 68 for addition of reagents and/or reagent containers 50 and, thereafter, returned to drawer 68. After the reagent inventory is adjusted by either adding reagents or reagent containers 50, the reagent drawer 68 is returned to the closed position. Similarly, the slide drawer 70 may be withdrawn in a horizontal, Y direction from the chassis 14 of the autostainer 10 to permit access to the slides 12 held by the slide racks 20 for removal or addition. This permits a user-convenient and independent access to the slides 12 and/or reagent containers 50 in the autostainer 10.

The drawers 68, 70 facilitated the exchange of slides 12 while limiting the impact of the exchange on the controlled environment within the processing space 18. In particular, the drawers 68, 70 permit the addition of slides 12, such as slides 12 carrying "stat" tissue specimens, quantities of reagent, and reagent containers 50 to the processing space 18, while limiting the impact of the exchange on the controlled environment within the processing space 18. It is appreciated that lid 16 is maintained in a closed condition, including instances in which the drawers 68, 70 are withdrawn from chassis 14, except for exceptional circumstances such as performing maintenance on autostainer 10. As a result, the lid 16 participates in isolating the processing space 18 from the environment surrounding the autostainer 10.

Figure 5:
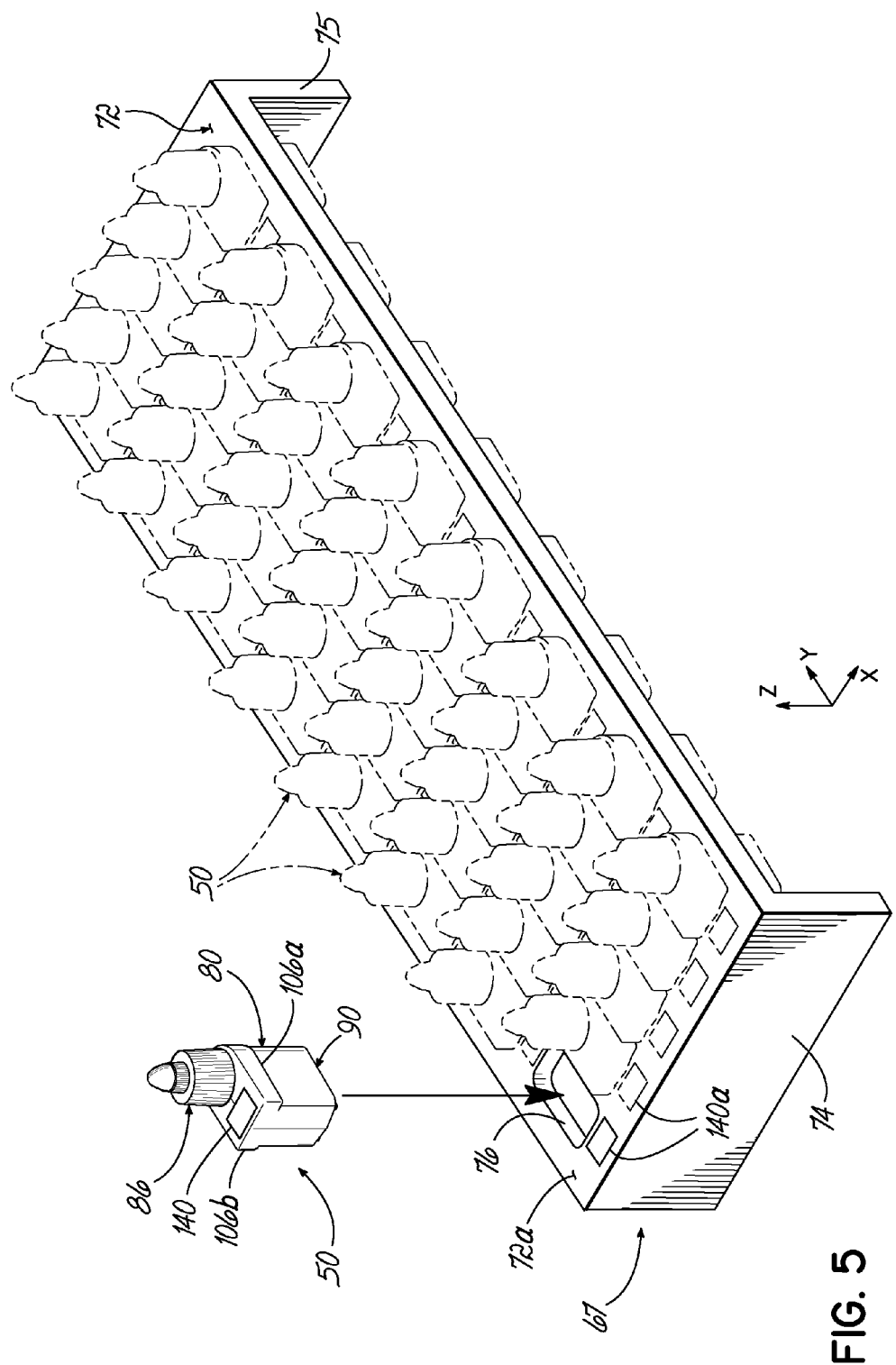
FIG. 5 is a perspective view of the reagent rack of FIG. 1.

With reference to FIG. 5 and in the illustrated embodiment, the reagent rack 67 includes a generally planar platform 72, a pair of spaced-apart supports 74, 75 projecting downward from opposite sides of the platform 72, and a plurality of apertures 76 each consisting of a substantially rectangular bore extending through the platform 72. Each of the apertures 76 is shaped and dimensioned to accept and hold the reagent containers 50 of the invention. Each reagent container 50 is suspended on a pair of outwardly-projecting flanges 106a, 106b that contact the platform 72 and prevent vertically downward movement of the container 50 relative to platform 72. The locations of the apertures 76 in the array are well-defined so that the reagent containers 50 are precisely positioned for reference by the control system 28.

The platform 72 of the reagent rack 67 is elevated by the spaced-apart supports 74, 75 so that each reagent container 50 is suspended above the underlying and confronting upper surface of the bottom of the autostainer 10. The elevation of reagent container 50 prevents application of a force that would otherwise displace the container 50 vertically relative to its aperture 76. Specifically, a base wall 90 (FIG. 6) of the reagent container 50 has a non-contacting relationship with the underlying and confronting upper surface of the bottom of the autostainer 10. Alternatively, the reagent rack 67 may permit reagent container 50 to contact the underlying upper surface of the bottom of the autostainer 10 if the applied vertical displacement force is nil or negligible. It is appreciated that the platform 72 may be supported by supports 74, 75 of differing configuration or otherwise supported in any manner that eliminates or minimizes any applied vertical displacement force.

With reference to FIG. 6, the reagent container 50 includes a reagent containment section 80 that holds a volume of a reagent within an internal reagent chamber 105, a hollow neck 82, a circular opening 84 at the top of the neck 82 providing access to the reagent containment section 80, and a closure 86 removably attached to the neck 82 for sealing the opening 84 against accidental spillage of the reagent and entry of contamination. The reagent containment section 80 includes an upper wall 88, the base wall 90, a rear wall 92 having a shallow V-shape, a pair of side walls 94 and 96, and a curved front wall 98. The rear wall 92, side walls 94, 96 and front wall 98 collectively constitute a tubular side wall which interconnects the upper wall 88 with the base wall 90. The corner edges 99, 100 at the intersection or junction of the side walls 94, 96 with the opposite edges of the rear wall 92 are rounded with a small radius. The reagent container 50 has a mirror symmetry about a plane bisecting the rear and front walls 92, 98. The upper wall 88 is vertically spaced from the base wall 90 along an imaginary vertical line 101 which passes through, and preferably is symmetrically disposed with respect to, the tubular neck 82. The imaginary vertical line 101 also preferably passes through the lowermost portion of the reagent chamber 105 at nadir 104, as discussed in more detail below.

With reference to FIGS. 6, 6A and 7 and according to one preferred aspect of the invention, the base wall 90 converges downwardly and inwardly from each of the side walls 94, 96, the rear wall 92 and the front wall 98 to define a concave, polyhedral cavity or well 102 communicating with the regent chamber 105. For reasons discussed hereafter, the existence of the well 102, and its spatial orientation with respect to the neck 84 and the imaginary line 101, increases the efficiency of reagent extraction from the reagent containment section 90. As shown in FIG. 7, the base wall 90 of the reagent container 50 includes four wall showing sections 80a-d that converge inwardly toward the nadir 104. The nadir 104 is a seam formed at the junction of the inner surfaces 80a' and 80d' of wall section 80a and wall section 80d, respectively. The nadir 104 is rounded with a narrow radius of curvature. Wall sections 80b and 80c taper inwardly from their respective boundaries with the side walls 94 and 96 for bounding the length of the nadir 104. In one embodiment, each of the inner surfaces 80b' and 80c' of wall sections 80b and 80c, respectively, tapers inwardly toward the nadir 104 at an angle of about 45° with respect to an imaginary vertical plane passing perpendicularly through nadir 104.

With continued reference to FIGS. 6, 6A and 7, well 102 of base wall 90 has a reduced horizontal cross-sectional area relative to the horizontal cross-sectional area of the reagent chamber 105, with the minimum horizontal cross-sectional area occurring near the nadir 104. The well 102 provides a reservoir of decreasing surface area as the volume of reagent within container 50 is expended by successive aspirations and the reagent fluid level within the reagent containment section 80 decreases below the lower horizontal edges of the walls 92, 94, 96, 98 toward the nadir 104. When the residual reagent no longer wets the walls 92, 94, 96, 98, the effective liquid surface area of the reagent in well 102 and facing the opening 84 decreases as the reagent is consumed. However, the enhanced fluid level or effective depth of the reagent in well 102 near the nadir 104 permits the decreasing volume of residual reagent to have a maximized effective depth for aspiration and delivery of the required volume by the reagent probe 38. In other words, the residual reagent in well 102 of reagent container 50 has a relatively high volume-to-surface ratio compared to conventional reagent containers having flat or relatively flat base walls. The high volume-to-surface ratio permits each reagent container 50 of the invention to be filled with less excess volume of reagent beyond the volume required for the staining run. The excess volume of reagent represents a minimum effective depth in reagent chamber 105 for which the reagent probe 38 can successfully aspirate reagent and remains in the container 50 after the reagent therein is dispensed during the staining run.

The reagent chamber 105 of reagent container 50, including well 102, holds a specific maximum volume of a reagent, typically about 15 ml, or any volume less than the maximum volume, which includes the excess volume described above. As the reagent is dispensed from the reagent container 50 by the autostainer 10, the fluid level or residual volume of the reagent in the interior 105 gradually drops. Eventually, enough reagent is dispensed from the interior 105 such that the only the residual reagent with reagent container 50 is confined in well 102 and has a volume greater than or equal to the excess volume. Because of the presence of well 102 and in one embodiment, reagent can be aspirated successfully from the reagent container 50 for an excess volume of residual reagent as small as about 0.1 ml. Therefore, reagent container 50 requires an excess volume of reagent in well 102 of only about 0.1 ml.

With continued reference to FIGS. 6, 6A and 7, the circular opening 84 in neck 82 is configured and dimensioned so that the reagent probe 38 can extend vertically into the reagent chamber 105 of the reagent containment section 80. Specifically, the center of the circular opening 84 is substantially aligned along the vertical imaginary line 101 with the midpoint 104' of the nadir 104 in well 102. A slight degree of misalignment between the center of the circular opening 84 and the midpoint of the nadir 104 may be tolerated so long as the reagent probe 38 can extend into a portion of well 102 near nadir 104. The tip of the reagent probe 38 will penetrate the upper surface of the reagent at a point in its vertical travel parallel to the Z axis of the robot toward base wall 90. Because the opening 84 is substantially aligned with the nadir 104, the tip of the reagent probe 38 will encounter an effective depth of residual reagent, as the reagent fluid level lowers to a point such that the residual reagent in entirely contained in well 102, that is sufficient for successful aspiration of a significant percentage of the total volume of reagent in the well 102, as well as close to 100% of the reagent in the entire reagent chamber 105. The reagent probe 38 is typically smaller diametrically than the opening 84. As a result, the reagent probe 38 may enter the opening 84 either parallel to the imaginary vertical line 101, or with a slight acute angle relative to line 101, and still travel in interior 105 toward and into well 102 proximate to the nadir 104.

With reference to FIGS. 7 and 8, the horizontal flanges 106a and 106b project outwardly from the exterior of the side walls 94, 96, respectively, and from portions of the front wall 98 of reagent container 50. As described above, the flanges 106a and 106b engage a top surface 72a of the platform 72 for suspending the base wall 90 of the reagent container 50 at or above the underlying upper surface of the bottom of chassis 14 when the reagent container 50 is supported within one of the receptacles 76 in reagent rack 67. As a result, the upper surface of the fluid, regardless of its fluid level within the reagent containment section 80, lies in a horizontal plane parallel with the X-Y plane of the robotic delivery system 22. The engagement between the flange 106 and the surface 72a of the platform 72 surrounding the receptacle 76 precludes the necessity for an adaptor or the like to hold the reagent container 50 in the rack 67 for use in the autostainer 10. It is understood that the specific structure of flange 106, illustrated in FIG. 6, is not intended to be limiting of the invention and various different flange structures may be utilized for supporting reagent container 160 in rack 67.

In one embodiment, the reagent containment section 80 and neck 82 are integrally formed as a single-piece of a polymeric material by a conventional manufacturing process, such as blow molding, so that the reagent containment section 80 has a degree of flexibility and is either optically translucent or transparent. In other embodiments, the reagent containment section 80 may also be fabricated from a relatively inflexible material, such as a glass, which is usually optically translucent or transparent. A portion of the front wall 98 includes a series of vertically spaced, horizontally disposed, volume indicia or graduations 108, which permit a visual determination of the approximate volume of reagent held by the reagent containment section 80 in those embodiments in which the reagent containment section 80 is not opaque. However, the invention is not so limited and the reagent containment section 80 may be opaque for those reagent dispensing applications in which visual determination of the fluid level of reagent is unnecessary or in which photosensitive reagents are stored.

With reference to FIGS. 6 and 8, the closure 86 of the reagent container 50 is a two-piece assembly having a dropper cap tip 112 and a nozzle cap 114. The dropper cap tip 112 includes a cylindrical side skirt 116, an annular collar 118, and a nozzle 120 having a fluid-directing passageway 122 with a dispensing orifice 132. An inner surface of the side skirt 116 includes a plurality of threads 123 that are threadingly engaged with complementary threads 124 provided on an outer surface of neck 82. The annular collar 118 includes a channel 126 with a frustoconical inner sealing surface 130 that engages a complementary frustoconical sealing surface 128 provided about the mouth of the opening 84. The threading engagement between the threads 123, 124 forces the frustoconical sealing surfaces 128, 130 into sealing engagement when the closure 86 is attached to the neck 82. If the reagent container 50 is used in the autostainer 10, the dropper cap tip 112 and the tip cap 114 are removed so that the opening 84 is not occluded. The nozzle cap 114 is threadingly received with a complementary threaded portion of the nozzle 120. The dropper cap tip 112 and the nozzle cap 114 may each include a plurality of parallel axially-directed ridges that ease manual removal from the neck 82.

In a preferred embodiment and with reference to FIGS. 7 and 8, a pair of protrusions 134, 136, illustrated as being rounded, project outwardly from the base wall 90. The protrusions 134, 136 are located proximate to the rear wall 92 and have a spaced relative to the side walls 94, 96. The protrusions 134, 136 and an exterior seam 107 of the base wall 90 are configured and positioned to contact a planar surface 110 when the reagent container 50 is placed thereupon. The seam 107 is located on the opposite side of base wall 90 from nadir 104 and has a similar length. The extent of the contacting engagement at the two points of protrusions 134, 136 and along the seam 107 lends lateral stability to the reagent container 50 when located on a planar surface 110, such as a laboratory benchtop. As a result, the reagent container 50 may be used in the autostainer 10 and may also be used independent of the autostainer 10. Even if used in conjunction with the autostainer 10, the reagent container 50 may be positioned on a planar surface 110 when not held in reagent rack 67. It is appreciated that the reagent container 50 of the invention includes a nadir 104 for improving reagent removal and is also capable of being self-supporting on planar surface 110 without relying upon a rack, such as reagent rack 67.

The reagent container 50 may also be used to deliver or dispense reagent manually from the reagent containment section 80 and, when not in use, container 50 would rest in an upright position on planar surface 110 supported thereupon by protrusions 134, 136 and seam 107. For manual delivery of reagent, the reagent container 50 is held in a tilted or an inverted orientation. In embodiments in which the reagent containment section 80 is flexible, a compressive force applied to the reagent containment section 80 reduces the volume of the reagent containment section 80 and urges a volume of reagent to enter fluid-directing passageway 122 for delivery from orifice 132. For those embodiments in which the reagent containment section 80 is not flexible, gravity causes a volume of reagent to be delivered from the dispensing orifice 132 of the inverted reagent container 50.

Figure 7A:
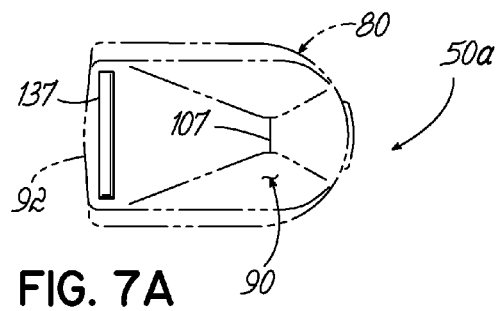
FIG. 7A is a bottom view of an alternative embodiment of the reagent container of the present invention.

In an alternative embodiment and with reference to FIG. 7A, a reagent container 50' may include a single surface-contacting projection 137 that replaces protrusions 134, 136 of reagent container 50 (FIG. 8). The projection 137 extends between the side walls 94, 96 and operates in conjunction with seam 107 to stabilize the reagent container 50' against tipping or otherwise deviating from an upright position, when container 50' is positioned on a flat surface, such as planar surface 110 (FIG. 8). Specifically, the seam 107 and the projection 137 provide two substantially parallel and spaced-apart lines of contact with a surface, such as planar surface 110.

Figure 9:
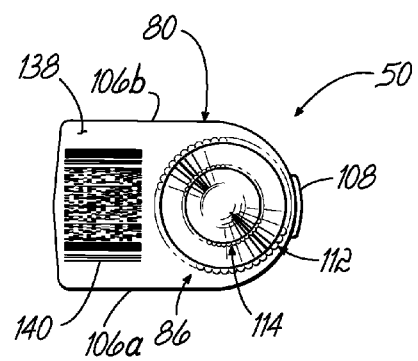
FIG. 9 is a top view of the reagent container of FIG. 6.

With reference to FIG. 9, the reagent container 50 includes a two-dimensional bar code 140. Bar code 140 may be positioned on any surface of container 50 accessible to a bar code reader, such as optical reader 144 (FIG. 1A), but is typically positioned on the flat upper surface 138 of the upper wall 88 and adjacent to the neck 82. The two-dimensional bar code 140 is any two-dimensional array of optically readable marks of any desired size and shape that are arranged in a reference frame of rows and columns. Specifically, the readable marks of the two-dimensional bar code 140 contain reagent information encoded in a high density format, as understood by those of ordinary skill in the art, and may include dots, characters or any symbol or symbols capable of encoding information. Among the numerous high density formats are matrix symbologies, such as Data Matrix and Maxicode, and two-dimensional stacked symbologies, such as Code 49 and PDF417. Code 49 is described, for example, in U.S. Pat. No. 4,794,239, Data Matrix code is described, for example, in U.S. Pat. Nos. 4,939,354, 5,053,609, and 5,124,536, Maxicode is described, for example, in U.S. Pat. Nos. 4,874,936, 4,896,029, and 4,998,010, and PDF417 is described, for example, in U.S. Pat. No. 5,243,655.

As known to one skilled in the art, reagent information that may be encoded into the two-dimensional bar code 140 includes, but is not limited to, the lot number of the reagent, the identity of the reagent, the expiration date, reagent volume, reagent incompatibilities, and the like. Such reagent information may be utilized for quality control and quality assurance documentation. It is further understood that two-dimensional bar codes 140a, similar to two-dimensional bar codes 140, may be applied to the reagent rack 67 adjacent to the appropriate reagent container 50, as shown in FIG. 5, and may contain readable reagent information.

With reference to FIG. 1A, the Z-head 24 of the autostainer 10 includes a two-dimensional optical reader 144, such as a charged coupled device (CCD) video camera or a CCD scanner, that is carried by the Z-head 24 of the X-Y-Z robotic delivery system 22. The reagent information associated with the two-dimensional bar code 140 is readable by optical reader 144. The optical reader 144 electro-optically scans the two-dimensional bar code 140 and generates a corresponding signal, which is provided to the control system 28 where the signal is decoded and the reagent information stored for future use. The ability to retrieve and decode information relating to the reagent from the two-dimensional bar code 140 eliminates the need to manually enter the reagent information when prompted by the control system 28.

Two-dimensional bar codes, such as two-dimensional bar code 140, may also be utilized in reagent packs (not shown) that contain various reagents in discrete containment wells. Such reagent packs for use with an autostainer, such as autostainer 10, are described in patent application Ser. No. 09/483,148, incorporated by reference above.

Figure 10:
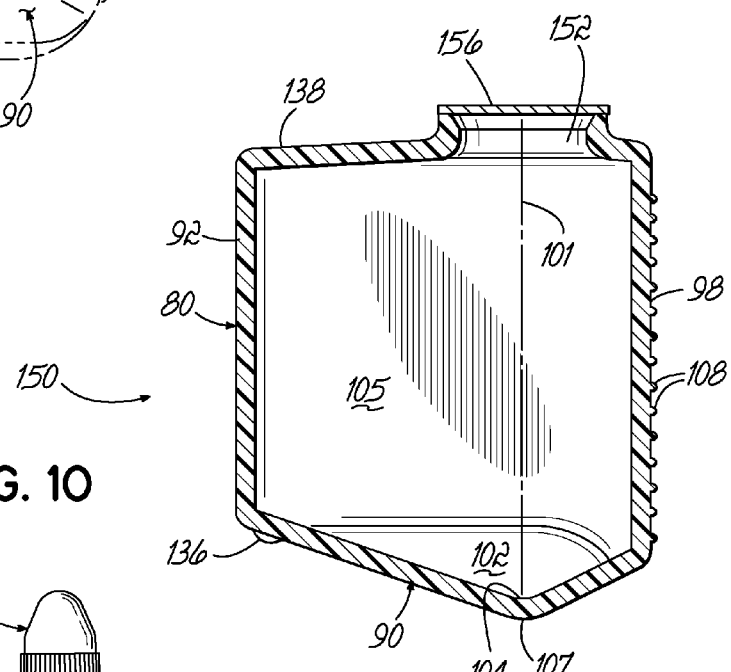
FIG. 10 is a cross-sectional view of another embodiment of a reagent container of the present invention.

With reference to FIG. 10 in which like reference numbers represent like features in FIG. 6, another preferred embodiment of a reagent container 150 of the present invention is shown. Reagent container 150 includes a circular opening 152 in the upper wall 138, an upwardly-projecting sealing lip 154 encircling the opening 152, and a frangible barrier 156 covering the entrance to the opening 152. The frangible barrier 156 may be formed, for example, from an aluminized polymer film. An outer rim of the frangible barrier 156 has a sealing engagement with the sealing lip 154 so that the reagent in the interior 105 of the reagent containment section 80 is isolated from the surrounding environment. The center of the circular opening 152 is substantially aligned along vertical imaginary line 101 with the midpoint of the nadir 104. The frangible barrier 156 is broken or penetrated prior to either manual use of reagent container 150 for the reagent held in or positioning reagent container 150 in autostainer 10 (FIG. 1) to afford access to the interior 105 for dispensing reagent therefrom.

Figure 11:
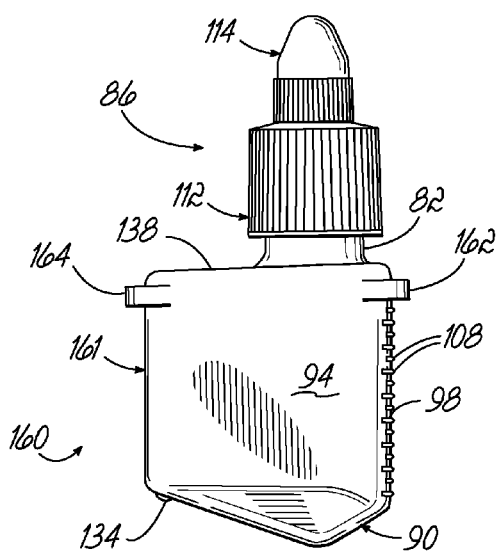
FIG. 11 is a perspective view of another embodiment of a reagent container of the present invention.

With reference to FIG. 11 in which like reference numbers represent like features in FIGS. 6-9, another preferred embodiment of a reagent container 160 of the present invention is shown. A reagent containment section 161 of reagent container 160 includes an outwardly-projecting pair of side flanges 162, 164 adapted to engage the top surface 72a of the platform 72 of rack 67 (FIG. 5) for suspending the base wall 90 of the reagent container 160 at or above the underlying upper surface of the bottom of the chassis 14 (FIG. 1) when the reagent container 160 is supported within one of the receptacles 76 in reagent rack 67. Side flange 162 is projects outwardly from the front wall 98 and flange 164 projects outwardly from rear wall 92 oriented with an opposite direction to side flange 162.

While the above description and accompanying drawings set forth various embodiments of the invention, it will be apparent to those skilled in the art that additions and modifications may be made without departing from the principles of the invention. Accordingly

What is claimed is:

1. A reagent container configured for use in an autostainer having a probe, the container comprising:
an upper wall having an access opening, a base wall, and a tubular side wall defining a reagent chamber, said tubular side wall including at least a first wall and an opposite second wall interconnecting the base and upper walls, said upper wall being spaced apart from said base wall along an imaginary line passing through said base and upper walls, said base wall converging inwardly and downwardly from said tubular side wall and defining a well having a reduced horizontal cross-sectional area relative to a horizontal cross-sectional area of said reagent chamber with a nadir that is spaced from each of said first and second walls and is located closer to said first wall than said second wall, said nadir and said access opening being aligned with each other along said imaginary line so that the probe entering said opening in a direction substantially parallel to said imaginary line is directed toward said nadir.

2. The reagent container of claim 1, wherein said upper wall includes a neck having a passageway extending substantially parallel to said imaginary line, said access opening being formed in said neck and being substantially coextensive with the cross-sectional area of said passageway.

3. The reagent container of claim 1, further comprising a pair of opposite side flanges extending outwardly from said tubular side wall of the container, with each of said side flanges being located a height between the upper wall and the base wall.

4. A reagent container and rack assembly configured for use in an autostainer having a probe, comprising:
a rack including:
a platform; and
at least one aperture formed in said platform;
at least one reagent container configured to be received within said at least one aperture formed in said platform and including an upper wall having an access opening, a base wall, and a tubular side wall defining a reagent chamber, said tubular side wall including at least a first wall and an opposite second wall interconnecting the base and upper walls, said upper wall being spaced apart from said base wall along an imaginary line passing through said base and upper walls, said base wall defining a well having a reduced horizontal cross-sectional area relative to a horizontal cross-sectional area of said reagent chamber with a nadir that is spaced from each of said first and second walls and is located closer to said first wall than said second wall, said nadir and said access opening being aligned with each other along said imaginary line so that the probe entering said opening in a direction substantially parallel to said imaginary line is directed toward said nadir; and
a pair of opposite side flanges extending outwardly from said tubular side wall of the container, with each of said side flanges being located at a height between the upper wall and the base wall and being configured to engage said platform to support said at least one reagent container relative to said platform.

5. The reagent container and rack assembly of claim 4, further comprising at least one support depending from said platform.

* * * * *